(12) United States Patent
Barnes

(10) Patent No.: US 7,393,635 B2
(45) Date of Patent: Jul. 1, 2008

(54) RIBOCLONING: RECOMBINANT DNA CONSTRUCTION USING PRIMERS WITH RIBO BASES

(75) Inventor: Wayne Morris Barnes, University City, MO (US)

(73) Assignee: DNA Polymerase Technology, Inc., University City, MO (US)

( * ) Notice: Subject to any disclaimer, the term of this patent is extended or adjusted under 35 U.S.C. 154(b) by 320 days.

(21) Appl. No.: 10/147,430

(22) Filed: May 16, 2002

(65) Prior Publication Data

US 2003/0215924 A1  Nov. 20, 2003

(51) Int. Cl.
*C12Q 1/68* (2006.01)
(52) U.S. Cl. .................... 435/6; 435/91.1; 435/91.2
(58) Field of Classification Search ........... 435/91.1, 435/91.2, 91.3; 536/23.1
See application file for complete search history.

(56) References Cited

U.S. PATENT DOCUMENTS

| | | | | |
|---|---|---|---|---|
| 5,658,731 | A | * | 8/1997 | Sproat et al. ............... 435/6 |
| 5,766,849 | A | * | 6/1998 | McDonough et al. ......... 435/6 |
| 5,824,517 | A | * | 10/1998 | Cleuziat et al. ............ 435/91.2 |
| 5,916,777 | A | * | 6/1999 | Kacian et al. .............. 435/91.1 |
| 6,251,590 | B1 | * | 6/2001 | Schweighoffer et al. ....... 435/6 |
| 6,358,712 | B1 | * | 3/2002 | Jarrell et al. .............. 435/91.1 |
| 6,380,377 | B1 | * | 4/2002 | Dattagupta ............... 536/24.3 |
| 2005/0014169 | A1 | * | 1/2005 | Latham et al. ............... 435/6 |

OTHER PUBLICATIONS

Chen et al. Universal restriction site-free cloning method using chimeric primers. Mar. 2002. Biotechniques vol. 32:517-520.*
Gal et al. Mol. Gen. Genet. vol. 260:569-573. 1999.*
Rashtchian et al. Analytical Biochemistry vol. 206:91-97.*
Cloning Fact Sheet. p. 1-4.*
DNA Cloining. p. 234-255. 2005.*

Booth, P.M. Buchman, G.W. & Rashtchian, A. (1994) Assembly and cloning of coding sequences for neurotrophic factors directly from genomic DNA using polymerase chain reaction and uracil DNA glyclosylase. Gene 146:303-308.
Chen GJ., Qiu N. & Page MGP (2002) Universal restriction site-free cloning method using chimeric primers, Biotechniques 32:518-524.
Coljee, V.W., Murray, H.L., Dohahue, W.F., & Jarrell, K.A. (2000) Seamless gene engineering using RNA- and DNA-overhang cloning. Nature Biotechnology 18:789-791.
Gal, J., Schnell, R., Szekeres, S., & Kalman, M. (1999) Directional cloning of native PCR products with preformed sticky ends (Autosticky PCR). Mol. Gen. Genet (1999) 260:569-573.
Jarrell, Kevin A.; Donahue, William; Mikhheva, Svetlana (2000) "Improved Nucleic Acid Cloning" PCT/US00/00189. WO 00/40715.
Oliner, J.D., Kinzler, K.W., & Vogelstein, B. (1993) In vivo cloning of PCR products in *E. coli*, Nucleic Acids Reasearch 21:5192-5197.
Rashtchian, A, Buchman, G., Schuster, D., & Berninger, M. (1992) Uracil DNA glycosylase-mediated cloning of PCR-amplified DNA: application to genomic and cDNA cloning. Anal, Biochem. 206:91-97.
Tillett, D., & Neilan, B.A. (1999). Enzyme-free cloning: a rapid method to clone PCR products independent of vector restriction enzyme sites. Nucleic Acids Research 27:e26I-iii.
Zhang, Youming; Buchholz, F., Muyrers, Joep P.P., & Stewart, F. (1998) A new logic for DNA engineering using recombination in *Escherichia coli*. Nature Genetics 20:123-128.

* cited by examiner

*Primary Examiner*—Gary Benzion
*Assistant Examiner*—Heather Calamita
(74) *Attorney, Agent, or Firm*—Sonnenschein Nath & Rosenthal LLP

(57) ABSTRACT

The present invention provides methods of linking nucleic acids without the use of restriction enzymes or any joining enzyme such as ligase. More specifically, the present invention provides methods for cloning or rearranging a double-stranded target DNA which is a PCR product into a double-stranded vector DNA which is a PCR product, said DNAs being amplified using primers that contain at least one ribonucleotide, preferably at or near the respective 3' ends of the primers, such that RNA-specific cleavage, preferably by RNAse A, will allow release of the primers to create long matching 3'-sticky ends.

25 Claims, 6 Drawing Sheets

Fig 1. Ribocloning

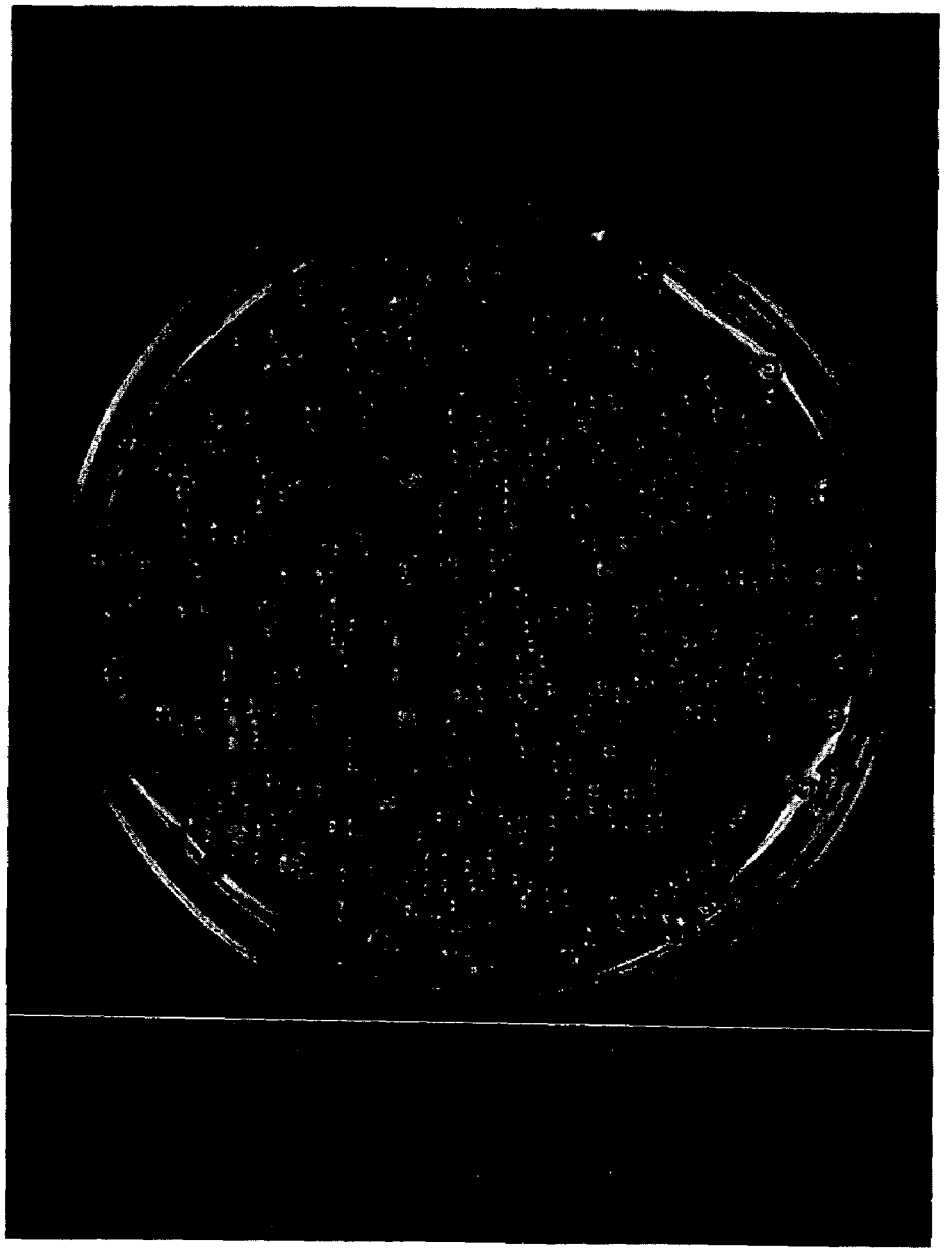
Fig. 3. Ribocloning a Ds-Red gene.

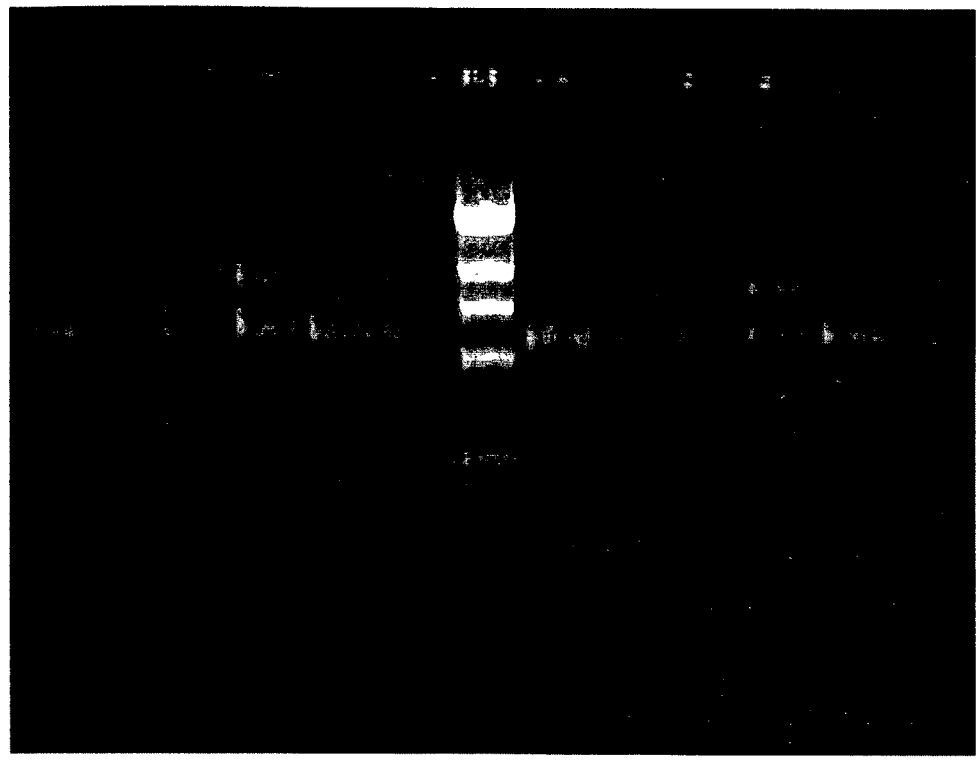
Fig. 4. Ribocloning the Taq gene

Fig. 5. Ribocloning the Taq gene without beads.

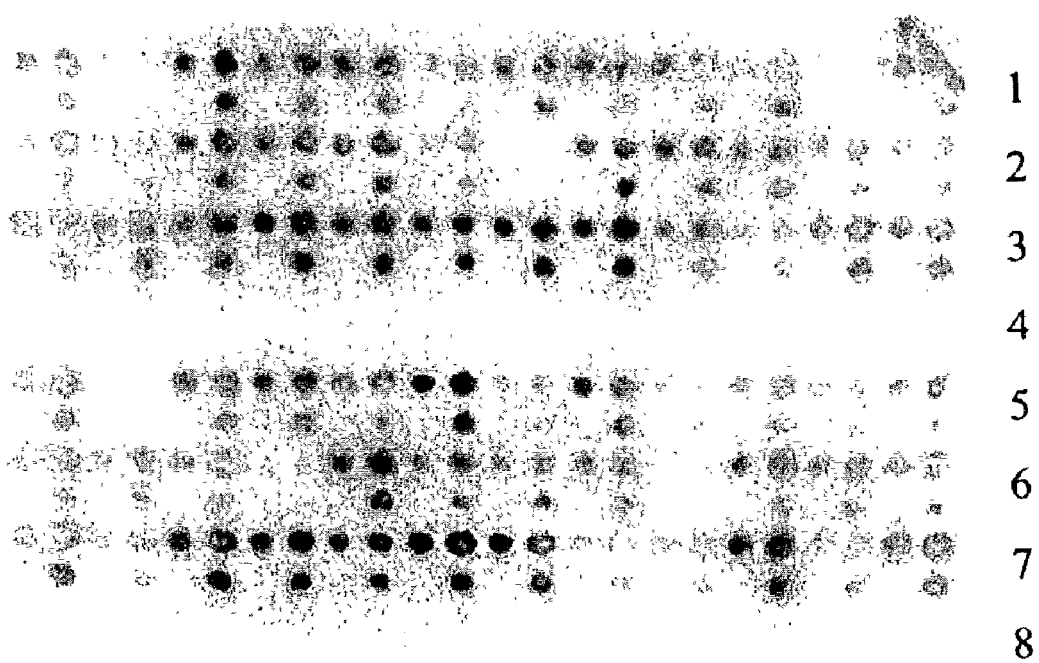
Fig. 6. Colony assay for thermostable DNA polymerase activity.

SEQUENCE LISTING

<160> NUMBER OF SEQ ID NOS: 14

<210> SEQ ID NO 1
<211> LENGTH: 25
<212> TYPE: DNA
<213> ORGANISM: Artificial Sequence

```
<220> FEATURE:
<223> OTHER INFORMATION: DNA with terminal 3'-ribo base

<400> SEQUENCE: 1
gtttaacttt aagaaggaga tatac                                    25

<210> SEQ ID NO 2
<211> LENGTH: 26
<212> TYPE: DNA
<213> ORGANISM: Artificial Sequence
<220> FEATURE:
<223> OTHER INFORMATION: DNA primer with 3'-terminal ribo base

<400> SEQUENCE: 2
gtttaacttt aagaaggaga tatatc                                   26

<210> SEQ ID NO 3
<211> LENGTH: 26
<212> TYPE: DNA
<213> ORGANISM: Artificial Sequence
<220> FEATURE:
<223> OTHER INFORMATION: DNA primer with 3'-terminal ribo base

<400> SEQUENCE: 3
gtggcgagaa aggaagggaa gaaagc                                   26

<210> SEQ ID NO 4
<211> LENGTH: 25
<212> TYPE: DNA
<213> ORGANISM: Artificial Sequence
<220> FEATURE:
<223> OTHER INFORMATION: DNA primer with 3'-terminal ribo base

<400> SEQUENCE: 4
gtatatctcc ttcttaaagt taaac                                    25

<210> SEQ ID NO 5
<211> LENGTH: 26
<212> TYPE: DNA
<213> ORGANISM: Artificial Sequence
<220> FEATURE:
<223> OTHER INFORMATION: DNA primer with 3'-ribo base

<400> SEQUENCE: 5
gctttcttcc cttcctttct cgccac                                   26

<210> SEQ ID NO 6
<211> LENGTH: 25
<212> TYPE: DNA
<213> ORGANISM: Artificial Sequence
<220> FEATURE:
<223> OTHER INFORMATION: DNA primer with 3'-terminal ribo base

<400> SEQUENCE: 6
gtttaacttt aagaaggaga tatau                                    25

<210> SEQ ID NO 7
<211> LENGTH: 49
<212> TYPE: DNA
<213> ORGANISM: Artificial Sequence
<220> FEATURE:
<223> OTHER INFORMATION: Partly pASK75 and partly T7 gene 10 ribosome
      binding site

<400> SEQUENCE: 7
actccctatc agtgatagag aaaagtttaa ctttaagaag gagatatac          49
```

```
<210> SEQ ID NO 8
<211> LENGTH: 53
<212> TYPE: DNA
<213> ORGANISM: Artificial Sequence
<220> FEATURE:
<223> OTHER INFORMATION: Partly phage T7 ribosome binding site,
      partly N-terminus ot Taq Pol I gene

<400> SEQUENCE: 8
gtttaacttt aagaaggaga tatatccatg agagggatgc tgcccctctt tga          53

<210> SEQ ID NO 9
<211> LENGTH: 52
<212> TYPE: DNA
<213> ORGANISM: Artificial Sequence
<220> FEATURE:
<223> OTHER INFORMATION: Partly phage f1 origin and partly N-terminus of
      Taq Pol I gene

<400> SEQUENCE: 9
gtggcgagaa aggaagggaa gaaagctcac tccttggcgg agagccagtc ct           52

<210> SEQ ID NO 10
<211> LENGTH: 42
<212> TYPE: DNA
<213> ORGANISM: Artificial Sequence
<220> FEATURE:
<223> OTHER INFORMATION: Partly pKD46, partly phage T7 ribosome binding
      site
<400> SEQUENCE: 10
tttgggaatt cgagctctaa ggaggttaat acgactcact at                      42

<210> SEQ ID NO 11
<211> LENGTH: 42
<212> TYPE: DNA
<213> ORGANISM: Artificial Sequence
<220> FEATURE:
<223> OTHER INFORMATION: T7 gene 10 leader region

<400> SEQUENCE: 11
agggagacca caacggtttc cctctagaaa taattttgtt ta                      42

<210> SEQ ID NO 12
<211> LENGTH: 42
<212> TYPE: DNA
<213> ORGANISM: Artificial Sequence
<220> FEATURE:
<223> OTHER INFORMATION: T7 gene 10 leader region

<400> SEQUENCE: 12
gaaaccgttg tggtctccct atagtgagtc gtattaacct cc                      42

<210> SEQ ID NO 13
<211> LENGTH: 42
<212> TYPE: DNA
<213> ORGANISM: Artificial Sequence
<220> FEATURE:
<223> OTHER INFORMATION: T7 gene 10 leader region

<400> SEQUENCE: 13
gtatatctcc ttcttaaagt taaacaaaat tatttctaga gg                      42

<210> SEQ ID NO 14
<211> LENGTH: 51
<212> TYPE: DNA
```

```
<213> ORGANISM: Artificial Sequence
<220> FEATURE:
<223> OTHER INFORMATION: Partly phage lambda, partly phage f1

<400> SEQUENCE: 14
ggatgcgtca tcgccattgc tccccgtggc gagaaaggaa gggaagaaag c          51
```

RIBOCLONING: RECOMBINANT DNA CONSTRUCTION USING PRIMERS WITH RIBO BASES

FIELD OF THE INVENTION

The present invention provides methods of linking nucleic acids without the use of restriction enzymes or any joining enzyme such as ligase. More specifically, the present invention provides methods for cloning or rearranging a double-stranded target DNA which is preferably a PCR product into a double-stranded vector DNA which is preferably a PCR product and methods for generating a hybrid double-stranded DNA comprising at least two target DNA sequences, all such DNA being amplified using primers that contain at least one ribonucleotide, preferably at or near the respective 3' ends of the primers, such that RNA-specific cleavage, preferably by RNAse A, will allow release of the primers to create long matching 3'-sticky ends.

BACKGROUND OF THE INVENTION

Recombinant DNA stems from the discovery of enzymes called restriction endonucleases or "restriction enzymes," that are capable of cleaving double stranded DNA at specific recognition sites, thereby producing DNA fragments that can be ligated to one another by ligase enzyme to generate "recombinant" molecules (see, for example, Cohen et al, Proc. Natl. Acad. Sci. USA 70:1293, 1973; Cohen et al., Proc. Natl. Acad. Sci. USA 70:3274, 1972; see also U.S. Pat. Nos. 4,740,470; 4,468,464; 4,237,224). The study of molecular biology has benefited greatly from the ability of scientists to join DNA fragments together in manmade arrangements for the purpose of experimentation or industrial production.

Molecular biology was further facilitated by the invention of the polymerase chain reaction (PCR), which allowed rapid in vitro amplification of selected DNA segments. This allowed for production of large amounts of replicated material that could subsequently be cleaved by restriction enzymes and ligated to other DNA molecules (see, for example, U.S. Pat. Nos. 4,638,195; 4,683,202; 5,333,675). Further advances of the PCR technique included the creation of a DNA polymerase having enhanced thermostability and polymerase mixtures having enhanced fidelity and length of product (U.S. Pat. No. 5,436,149). PCR products can be cloned using restriction enzymes, if the primers are made longer to incorporate the desired restriction site, if said site is not present in the PCR product or cutting at it can be suppressed, and if the vector has a similar matching restriction site. It is important to carry out a purification of the PCR product to at least remove dNTPs and/or polymerase before digestion by restriction enzymes, especially for 5'-sticky ends, since they can be filled in by said left-over DNA polymerase.

A way to clone PCR products without restriction enzymes, and also using RNA/DNA primers, has been recently described [Chen G J., Qiu N. & Page MGP (2002) Universal restriction site-free cloning method using chimeric primers, Biotechniques 32:518-524]. This method still uses ligase, and the ribo base cleavage is not enzymatic, but rather by the use of rare-earth metal ions, which are not as efficient, convenient, or specific as RNAse enzyme.

Ways to clone the PCR products without the use of ligase have been developed. For instance, TOPO (™Invitrogen)—cloning utilizes special vectors with adjacent sites for Vaccinia virus topoisomerase, and said vector is pre-activated with topoisomerase. If the PCR product has terminal extra As, and no 5'-phosphates, it can be cloned into this vector conveniently, at a site between the two topoisomerase recognition sequences. The present invention has no requirement for any specific vector or even the site of cloning within any vector, except that the vector must preferably be amplifiable by PCR using primers at the cloning site. Another example of a non-ligase cloning method utilizes terminal homology similar to the present invention, although usually twice as long. Special E. coli strains which highly express the recET system, or any yeast strain (if the vector is a yeast vector) can then be used to recombine target and vector. This system is not very efficient, and is prone to recombination and rearrangements at other homologous or repeated sites on the vector and/or target molecules, rather than just at the desired and small terminal homologies.

Thus despite these advances, there is substantial room for improvement. The use of restriction enzymes requires that the segment of DNA being digested have the particular restriction site only at desired locations—that is to say, a particular DNA base sequence (restriction site) is necessary to enable the restriction enzyme to digest the particular piece of DNA, yet the restriction sites must be rare or preferably non-existent within the vector or target, lest they be cut up too much to put together in the desired arrangement. Often, 2 vector or 2 target molecules will join, often in the wrong orientation, whereas the desired product is usually one vector and one target with one desired orientation.

Therefore, molecular biology could benefit from the development of improved systems of cloning and joining of DNA molecules. Of particular interest would be a system that would allow DNA joining without the use of, or indeed any regard for, restriction enzymes or restriction sites, provide for efficient joining, provide an increase in yield and specificity of the desired product, decrease the cost of molecular biological experiments, and be generally useful for the joining of DNA sequences having a wide variety of sequences. Optimal systems would even provide for directional joining (i.e., joining in which the DNA molecules to be linked together will only link to one another in a single orientation).

SUMMARY OF THE INVENTION

Among the objects of the present invention are methods for linking nucleic acids together. In particular, the present invention provides methods for producing DNA target molecules that may be easily and directly inserted into vector molecules or attached to other DNA target molecules, all without the use of restriction enzymes, ligase, or topoisomerase, nor with any regard for restriction site sequences.

The inventive system provides techniques and reagents for generating target molecules with 3'-single-strand overhangs, and further provides the tools and methods for preparing vector or other target DNA molecules with matching complementary 3'-single-strand overhangs, allowing the efficient and specific linking of DNAs such as target(s) and vector to each other in desired orientation and location. The length and sequence of the overhangs can be varied according to the desires of the practitioner, and do not need to be fully complementary. Therefore, one aspect of the invention provides a method of cloning a double-stranded target DNA into a double stranded vector DNA, said method comprising:

a) generating by PCR a double-stranded target DNA molecule using hybrid "riboprimers" as the two PCR primers, which riboprimers are not all DNA, but rather include at least one ribonucleotide, most conveniently at their respective 3' ends, and preferably rC or rU, and which PCR primers comprise sequences complementary to the ends of vector DNA sequences, which is to say at the desired site of recombination. The resulting PCR product will have incorporated near each 5'-end a single (or more) ribonucleotide at a position preferably some 25 bases in from each 5' end;

b) if the target does not already have homology to the PCR riboprimers, i.e. complementarity to the vector cloning site, then the PCR amplification reaction can be carried out in the presence of one or two bracketing "band-aid" oligomers (for example, 50 mers) which comprise one strand of the desired end-point recombined structure consisting of adjacent sequences complementary to the ends of said target (for example, 25 bases) and vector DNA (for example, 25 bases). The band-aid primers are used at such low concentration that it is often helpful to employ unusually long PCR extension times, at annealing temperatures, in order to allow for slow kinetics of band-aid annealing. Alternatively, but less conveniently, successive PCR amplifications may be performed, in which the band-aid primers are oriented so that they can function at the first PCR amplification and are preferably at least 95% removed or diluted before the second PCR amplification which uses the riboprimers. If the template for the target already contains the sequences to match the riboprimers, the band-aid primers are of course unnecessary;

c) exposing the target DNA to RNA-cleaving conditions that do not cleave DNA, preferably by the use of bovine pancreatic RNAse A enzyme, that result in the single-strand cleavage of said riboprimers at the point of the single (or more) ribonucleotide rC or rU, followed by heating at a temperature that melts the PCR primers from said target DNA, preferably followed by removal of the PCR primers and any uncleaved DNA, thereby generating target DNA with 3'-overhangs;

d) similarly providing a vector DNA with circa 25-base 3'-overhangs, including amplification specified by PCR riboprimers that are completely or mostly complementary to the PCR riboprimers used for the target, and, if the riboprimers do not already match the template, including the similar use of band-aid primers; and e) incubating said target DNA and said vector DNA under conditions that result in annealing of the complementary ends thereof. The joined ends are so stable that they are ready for transformation into the host cells without further enzymatic processing in vitro.

Furthermore, the amplification by PCR can be catalyzed by any one of a number of DNA polymerases and mixtures of DNA polymerases, including, but not limited to, Vent, Deep Vent, Pfu, Pwo, Klentaq1, KlentaqLA, TaqLA, Taq, KOD, and further mixtures thereof Archeal DNA polymerases (such as Vent, Deep Vent, Pfu or Pwo) which cannot cross a ribonucleotide on the template must include a small admixture of a polymerase which can cross the ribonucleotide (such as Klentaq1 or Taq). Additionally, the vector DNA can be from any form of replication, including but not limited to, bacterial, viral, yeast, plant, or animal cell vectors.

The annealed molecules have discontinuities such as a nick, a nick with a slight overlap, or a gap on each strand, about 25 bases apart. These discontinuities are automatically and preferably repaired in vivo (intracellularly) after transformation, without special arrangement by the technician, and without the choice of any particular host cell recombination capacity or noncapacity, since the repair does not require recombination. Nevertheless it is possible to repair the discontinuities in vitro using methods well known in the art, such as nick-translation catalyzed by *E. coli* DNA polymerase I, followed by, or combined with, ligase treatment. The structure of the recombed product is ideally suited for nick translation; the long 3'-sticky ends result in a structure that is made even more stable by the process of nick translation, which would move the nicks farther and farther apart on the DNA and leave them ever more suitable as substrates for any DNA ligase.

It is another object of the present invention to provide methods of cloning a double-stranded target DNA into a double stranded vector DNA and methods of generating hybrid DNA molecules using the methods described herein, wherein the riboprimers additionally comprise biotin molecules at their respective 5' ends. In one embodiment, following the step of cleavage at the one or more ribo base comprised by the riboprimers, the cleaved target or vector DNA, incompletely cleaved or uncleaved target or vector DNA, and the primers are incubated with paramagnetic streptavidin beads, following which the completely cleaved target or vector DNA is separated from biotin-containing primers and biotin-containing uncleaved target or vector DNA which remain attached to the streptavidin beads. Alternatively, the incubation with streptavidin beads may be performed prior to the cleavage step, thus allowing for the cleavage to occur on the beads, but this is not recommended due to poorer performance.

In the methods described herein the one or more ribonucleotide within or preferably at the 3' end of the primers can be selected from the group consisting of: riboC, riboU, riboT, riboA, riboG or riboI. The RNA-cleavage conditions that result in the cleavage of riboprimers from desired DNA molecules can be performed using alkali, but this causes denaturation of the subject DNA, which must therefore be neutralized and reannealed to reconvert the DNA to the double-stranded form.

It is preferable to use an RNAse capable of cleaving a bond between a particular 3'-end ribonucleotide comprised near the 5'-end of the PCR product and the adjacent deoxynucleotide. In one embodiment, the RNAse comprises RNAse A, which can cleave at single bases of riboU and riboC within double-stranded PCR products, and the use of low salt is key. It is a surprising aspect of the invention that RNAse A can do this, since RNAse A is well known as a single-strand specific RNAse. It is important for the efficiency of the method that the RNAse not be contaminated with any other nucleases, such as DNAse II.

RNAse $T_1$, would be appropriate for riboG.

After the RNAse cleavage, mild heating releases said primers from the DNA molecules without denaturing the double-stranded PCR products. Furthermore, the vector, or portion of a vector, can be any commercially available vector, or desired suitable portion of a vector, that can be amplified by PCR.

Band-aid primers may be on either strand. If on one strand (3'-ends pointing toward the target DNA, same as the PCR riboprimers) they will also serve to prime extension on the intended template, albeit, if included at the recommended very low (2-10 nanomolar) concentration, less efficiently than the PCR riboprimers. When band-aid primers are on this strand, the final PCR product will be contain them in some small proportion, and this proportion will not contain the ribonucleotide(s) supplied by the riboprimers. If the band-aid primers are on the other strand (3'-ends pointing away from the target DNA), they will at first and at early cycles of the PCR only serve as a short template, and the only template, for the PCR primers, which will be extended over the band-aid primers. Then the extended PCR primers will be able to initiate extension on the actual desired target at the second and later cycles of the PCR. Because all of the PCR product is expected to contain the ribonucleotide(s) from the riboprimers, this method (band-aid primers pointing away from the target) is preferred. It is of little consequence, and the method still works, if the band-aid primers are a mixture of the two types, i.e. mutually on the very same strand. Band-aid primers may be of any length, and may be double-stranded, but preferably they have at least 20 bases of sequence overlap (preferably 24-26 bases) with the PCR product to be amplified at one of their ends, and a similar amount of sequence homology to the PCR riboprimers somewhere within them, distal to the amplified PCR span, such as at their other end.

Furthermore, the use of band-aid primers at low (ca. 3-10 nanomolar) concentration may be extended by including during the PCR reaction several overlapping primers (such as 40-60 mers) at similarly low concentration, to build up significant lengths of novel sequence onto the vector or target. This principal of low concentration (about 20 times lower than Stemmer et al.) and long annealing/extension time, preferably about 20 minutes (which is 20-40 times longer than Stemmer et al.), may be extended, by the use of dozens of overlapping primers, to constitute an improvement to the method of synthesis and assembly of entire genes. [Stemmer, W. P. C., Crameri, A., Ha, K. D., Brennan, T. M., & Heyneker, H. L. (1995) Single-step assembly of a gene and entire plasmid from large numbers of oligodeoxyribonucleotides. Gene 164:49-53. See also Chen, G.-Q., Choi, I., Ramachandran, B. & Gouaux, J. E. (1994) Total gene synthesis: Novel single-step and convergent strategies applied to the construction of a 779 base pair bacteriorhodopsin gene. JACS 116:8799-8800. See also Dillon, P. J., & Rosen, C. A. (1990). a rapid method for the construction of synthetic genes using polymerase chain reaction. Biotechniques 9:298-299.]

The present method is useful for one or more ribo bases throughout the primer. An advantage to internal ribo bases is that, upon cleavage at 2 locations, the fragments of primer remaining will not tend to compete with productive recombinant annealing. Primer left over from the PCR will be similarly degraded. Only one ribo base per PCR primer is the most challenging special case of the method, yet it is the case demonstrated in the examples, for the possibly temporary reason of cost of manufacture of oligos with internal ribo bases. Taking for example a case of 2 ribonucleotides, with one at the 3'-end, and another in about the middle of a primer, the cost is currently six times higher than with a single 3'-riboC, due in part to the need to use RNAse-free conditions during manufacture. Addition of a 5'-biotin is currently expensive also, but it merely triples the cost (3.3x). Besides being less expensive, the use of 5'-biotin ends has the advantage of positive purification of sticky-ended products, as described here with the use of streptavidin beads. If expense is not a consideration, one could combine these approaches. Two ribobases per primer, without 5'-biotin, could be used for the PCR and then the primers cleaved to 12-13 bases with RNAse A. Separately, 5'-biotin, all-DNA primers could be synthesized and added, and annealed, for the purpose of streptavidin bead purification of sticky-ended targets or vectors. If this is done in series with each end at a time, each sticky end could be positively selected.

Other objects and features will be in part apparent and in part pointed out hereinafter.

DETAILED DESCRIPTION OF THE INVENTION

The following description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

The listed abbreviations and terms, as used herein, are as follows:

bp is the abbreviation for base pairs.
kb is the abbreviation for kilobase (1000 base pairs).
nt is the abbreviation for nucleotides.
"overlap" means DNA sequence homology or complementarity, as appropriate.
10 nM means 10 nanomolar
Taq is the abbreviation for *Thermus aquaticus*.
Pfu is the abbreviation for *Purococcus furiosus*.
Vent is the abbreviation for *Thermococcus litoralis* DNA polymerase.
KOD is the abbreviation for hyperthermophilic archaeon *Pyrococcus kodakaraensis* KOD1 (KOD DNA polymerase)
Deep Vent DNA polymerase is purified from an archael, thermophilic bacterium by New England Biolabs, Inc.
"Klentaq1" is a trademark for Klentaq-278 which is a DNA polymerase having substantially the same amino acid sequence as *Thermus aquaticus* DNA polymerase, but excluding the N-terminal 278 amino acids, ± one residue as claimed in U.S. Pat. No. 5,616,494, incorporated herein by reference.
"LA PCR" is Long and Accurate PCR, which is PCR using an unbalanced mixture of two DNA polymerases, as claimed in U.S. Pat. No. 5,436,149.
"KlentaqLA" is an unbalanced mixture of two DNA polymerases, wherein the major component is the thermostable DNA polymerase known as Klentaq1 or Klentaq278 and lacking 3'-exonuclease and the minor component is at least one DNA polymerase exhibiting 3'-exonuclease activity, as claimed in U.S. Pat. No. 5,436,149. KlentaqLA is commercially available from Clontech (Cat. No. 8421-1) and from Sigma (Cat. No. D6290). In the examples shown, the minor component is "Deep Vent" DNA polymerase.
"TaqLA" is an unbalanced mixture of two DNA polymerases, wherein the major component is full-length Taq DNA polymerase as the thermostable DNA polymerase lacking 3'-exonuclease activity and the minor component is at least one DNA polymerase exhibiting 3'-exonuclease activity, as claimed in U.S. Pat. No. 5,436,149, incorporated herein by reference. In the examples shown, the minor component is "Deep Vent" DNA polymerase.
"Thermostable" is defined herein as having the ability to withstand temperatures up to at least 95° C. for many minutes without becoming irreversibly denatured and the ability to polymerize DNA at optimum temperatures of 55° C. to 75° C.
PCR primers are usually present at 20 pmoles per 100 ul (0.2 micromolar), and serve to direct in vitro amplification to the DNA sequence specifically between them on a template.
"Band-aid" primers usually contain adjacent sequence of circa 25 nt each, from the ends of the target and the vector. They are used to bridge the PCR primers onto the target to be amplified.
"PCR" is the polymerase chain reaction which is a process in which replicate copies are made of a target polynucleotide using one or more primers, and a catalyst of polymerization, such as a DNA polymerase, and particularly a thermally stable polymerase. Generally, PCR involves repeatedly performing a "cycle" of two or three temperature steps: "melting", in which the temperature is adjusted such that the DNA dissociates to single strands, "annealing", in which the temperature is adjusted such that oligonucleotide primers are permitted to match their complementary base sequence using base pair recognition to form a duplex at one end of the span of polynucleotide to be amplified; and "extension" or "synthesis", which may occur at the same temperature as annealing, or in which the temperature is adjusted to a slightly higher and more optimum temperature. Oligonucleotides that have formed a duplex (which have primed onto a template strand) are elongated with the provided DNA polymerase. This cycle is then repeated until the desired amount of amplified polynucleotide is obtained. Methods for PCR amplification are taught in U.S. Pat. Nos. 4,683,195 and 4,683,202.

In vitro processes of producing replicate copies of the same polynucleotide, such as PCR, are collectively referred to herein as "amplification" or "replication." For example, single or double stranded DNA may be replicated to form another DNA with the same sequence. RNA may be replicated, for example, by a RNA directed RNA polymerase, or by reverse transcribing the RNA using a reverse transcriptase or a DNA polymerase exhibiting reverse transcriptase activity and then performing a PCR amplification. In the latter case, the amplified copy of the RNA is a DNA (known as "copy DNA:, "complementary DNA", "cDNA" or RT-PCR product) of the correlating or homologous sequence.

"Amplimer" is a term for the span of DNA that is amplifed by the PCR process, a.k.a. a "PCR product".

"Riboprimer" is a form of PCR primer that contains at least one ribonucleotide instead of DNA, most conveniently at the very 3'-end.

"Ribocloning" refers to the use of riboprimers to specify amplimers which can be recombined by the present method.

"Specificity" in PCR amplification refers to the generation of a single, "specific," PCR product with the size and sequence predicted from the sequences of the primers and the genomic or transcribed region of nucleic acid to which the primers were designed to anneal in a base-complementary manner. "Nonspecific" PCR product has a size or sequence different from such prediction. A "target nucleic acid" is that genomic or transcribed region of nucleic acid sought to be replicated, generally the ends of which are base-complementary (with proper orientation) to primers included in a complete set of PCR reagents. A primer refers to a nucleic acid sequence, which is complementary to a known portion of a target nucleic acid sequence and which is necessary to initiate synthesis by DNA polymerase. A primer, as used herein includes riboprimers unless the context precludes it. "Proper orientation" is a term used to indicate that the two primers anneal to opposite strands of double-stranded target nucleic acid with their 3' ends pointing toward one another on the sequence. Such primers are said to target the genomic or transcribed sequence to the ends of which they are base-complementary. An "appropriate temperature," as referred to in the claims in regard to the PCR amplifications, indicates the temperature at which specific annealing between primers and a target nucleic acid sequence occurs.

"*Thermus aquaticus* DNA polymerase" and "Taq DNA polymerase" are used interchangeably to refer to heat stable DNA polymerases from the bacterium *Thermus aquaticus* and include all Taq mutants, natural and synthesized.

The procedures for the use of PCR to replicate nucleic acid sequences disclosed herein are known to those skilled in the art. See generally Fredrick M. Ausubel et al. (1995), "Short Protocols in Molecular Biology," John Wiley and Sons, and Joseph Sambrook et al. (1989), "Molecular Cloning, A Laboratory Manual," second ed., Cold Spring Harbor Laboratory Press, which are both incorporated by reference.

As used herein, the terms "complementary" or "complementarity" refer to the pairing of bases (purines and pyrimidines) that associate through hydrogen bonding base-pair recognition in double stranded nucleic acid. The following base pairs are complementary: guanine pairs with cytosine; adenine with thymine; and adenine with uracil. As used herein complementariy and complementary include complete and partial complementarity.

As used herein, "sequence" means the linear order in which monomers occur in a polymer, for example, the order of amino acids in a polypeptide or the order of nucleotides in a polynucleotide.

As used herein, "riboprimer" refers to a primer that comprises at least one ribonucleotide, usually at the 3' end, but also usefully at one or more positions from 5 to 26, preferably at one or more positions from 13 to 26, with usefulness but steadily decreasing preference with each base farther than 26 from the 5' end.

The terms "recombine", "anneal", and "link" are used interchangeably herein to refer to a process of joining two or more nucleic acids at their ends, which are in this invention arranged and adjusted to be complementary (and in this invention unusually long) sticky ends, without the use of accessory enzymes to catalyze the joining. It is understood that transformed cells are able to complete the joining by the use of various DNA repair enzymes intracellularly.

The term "target DNA" as used herein, refers to a [double-stranded] DNA sequence that is to be cloned into a [double-stranded] vector (so-called because it comprises a replicon) or that may be joined with additional [double-stranded] DNA sequences. Accordingly, the present invention provides novel methods for joining at least two DNA sequences. Such methods are useful for cloning a target DNA molecule into a vector or for recombining two or more target DNA sequences. In addition, the methods disclosed herein care little about the location of insertion within the vector, and avoid the use of restriction enzymes, ligase or topoisomerase, thereby contributing to the generality, accuracy and efficiency of nucleic acid cloning and rearrangement.

The term "vector" refers do a [double-stranded] DNA sequence that carries a replicon and a suitable selective marker that will allow selection of transformants in the form of life that that the replicon and marker are expressed in. More generally, the term "vector" refers to a DNA sequence that will allow the replication or expression of an attached target DNA, whether in vivo or in vitro. As used herein, the term "vector" may only include sequences, such as extensive homology or restriction sites, suitable for a separate step of recombination that would eventually lead to the desired DNA structure.

In one embodiment, the present invention provides methods of cloning a double-stranded target DNA into or onto a double-stranded vector, wherein said methods comprise:

a) generating a double stranded target DNA molecule by extension of primers, usually a matching pair of primers, from opposite strands, which bracket the target on the DNA sequence, wherein said primers are riboprimers and comprise sequences complementary to said target DNA and are present in the target DNA amplification reaction; and separately and similarly generating a vector DNA molecule using similar primers having sequences which define the ends of and direct the specific formation of the vector DNA, and are present in the vector DNA amplification reaction. To allow for eventual annealing of the ends of the target and vector DNA, one of the target riboprimers and one of the vector riboprimers are completely and exactly complementary to one another, or they share enough complementary homology, generally known to be about 12 bases, to anneal together stably in solution without the need of catalysis by any enzymes. A similar homology is designed to exist for the second target riboprimer and the second vector riboprimer. Riboprimers are PCR primers that contain at least one ribonucleotide, usually at their respective 3' ends;

b) exposing the target and/or vector DNA to conditions that specifically cleave RNA and result in the cleavage of said riboprimers at the position of their one or more ribonucleotides even though surrounded by DNA, usually double-stranded DNA, thereby generating cleaved target DNA with a nick about 25 bases (preferred range 12-26 bases) from each 5' end;

e) melting off the 12-15 base fragments under conditions that do not melt the bulk double-stranded PCR product DNA, thus leaving a 12-26 base 3'-single strand at each end;

d) combining the target DNA and vector DNA, or two or more target DNAs, at near equimolar amounts; and e) incubating said cleaved target DNA and said vector DNA and/or other target DNAs under conditions that result in annealing of the complementary ends thereof Complementarity between target and vector is often achieved through the use of bracketing oligonucleotides that contain overlap between the target and the vector. These bracketing oligonucleotides (referred to herein as "bandaid" primers) are generally only employed in initial cycles of PCR to create target DNA sequences with ends complementary to the ends of the vector, and thus are used in smaller quantities than riboprimers. Preferably, amplification is performed using about 20 pmoles of each riboprimer and ½ to 1 pmole of each bandaid primer per each 100-150 ul of reaction volume. In one embodiment, bandaid primers are about 50 nucleotides long, comprising about 25 nucleotides from the target ends and about 25 nucleotides from the vector ends; however, a skilled artisan can select other lengths as well that would also allow successful priming of DNA synthesis. For the synthesis of DNA/RNA hybrids as described herein, any DNA polymerase known in the art that is capable of extending from a riboprimer can be used, which is all of them, as far as we know, since extension from an RNA primer is a natural part of the initiation of DNA syntheses in cells. However, some DNA polymerases, particularly those from the Archea, cannot cross the ribonucleotides as template when they come back the other way on the next PCR cycle. Complete crossing of the ribonucleotides as template is a necessary part of this method, so it is recommended to include at least some Taq or Klentaq in what would therefore be a mixture of DNA polymerases, to ensure crossing at these positions to complete each strand during a PCR cycle.

The riboprimers that are used to amplify the target DNA sequence contain at least one ribonucleotide at or near their respective 3' ends. Ribonucleotides can be selected from the group consisting of riboC, ribo U, ribo T, riboA, riboG, and riboI. The particular ribonucleotide is chosen based on optimal efficiency of commercially available ribonucleases. Pancreatic RNAse A, catalog numbers 2270 and 2272 from Ambion is particularly effective, but can only cleave at rU, rT, and rC. The riboprimers are preferably about 24-26 nucleotides in length, however their precise length is optional and can be chosen by a practitioner. Generally, the riboprimer length is from about 20 nucleotides to about 30 nucleotides. In addition, the nucleotide sequence of each of the riboprimers is selected by the practitioner and need not be fully complementary to the sequence of the target DNA. As is known in the art, perfect complementarity is not required for successful extension of primers and resulting DNA synthesis, nor for successful annealing.

During PCR, the 5' end of the primer does not need to be paired at all to the DNA being amplified; thus adding nucleotides to the 5' end of the primer may be useful in generating target DNAs that contain additional sequences. For instance, the bandaid primers that are used herein comprise sequences complementary to the target DNA at 3' ends and sequences complementary to the vector DNA at 5' ends, thus allowing for addition of vector end sequences on both ends of the target DNA. Other considerations of primer design are well known in the art (see, for example, Newton et al., (des), PCR: *Essential Data Series*, John Wiley and Sons, New York, N.Y., 1995; Dieffenbach (ed), *PCR Primer: a Laboratory Manual*, Cold Springs Harbor Laboratory Press, Cold Springs Harbor, N.Y. 1995; White et al. (eds), *PCR Protocols: Current Methods and Applications; Methods in Molecular Biology*, The Humana Press, Totowa, N.J., 1993; Innis et al., *PCR Protocols: A Guide to Methods and Applications*, Academic Press, San Diego, Calif., 1990; Griffin et al. (eds.), *PCR Techology, Current Innovations*, CRC Press, Boca Raton, Fla., 1994, each of which is herein incorporated by reference). For instance, it is often desirable for approximately 50% (range 45-55%) of the hybridizing residues to be Gs or Cs.

Riboprimers that contain at least one ribonucleotide, preferably at their 3' ends, may be prepared by any technique available in the art. For example, such riboprimers may be chemically synthesized. Such riboprimers are commercially available from companies such as, e.g., DNAgency and Integrated DNA Technologies (IDT), (http://www idtdna.com) which will synthesize primers according to a practitioner's request. Alternatively, riboprimers may be generated by ligating at least one ribonucleotide to the 3'-end of a DNA sequence that is to be used as a primer (see, for example, Moore et al., *Science* 256:992, 1992; Smith (ed), *RNA: Protein Interactions, A Practical Approach*, Oxford University Press, 1998, which are incorporated herein by reference).

Riboprimers that are preferably used comprise only one ribonucleotide at their 3' ends. While the presence of only one ribonucleotide in each riboprimer does not decrease the efficacy of priming and/or cleaving of said riboprimers from the target DNAs, synthesis of riboprimers with only one ribonucleotide is more cost-effective than synthesis of primers with more than one ribonucleotide. In one embodiment of the present invention, a ribonucleotide used for the methods of the present selection may be selected from riboC, riboG, riboA, riboU, riboT, and riboI. In a preferred embodiment, the ribonucleotide comprises riboC or riboU.

Following the generation of a double-stranded target DNA that contains at least one ribonucleotide on each strand, the solution comprising the target DNA may be precipitated with PEG in order to remove the unincorporated primers, followed by resuspension of the target DNA in a low salt solution (such as 5 mM Tris, 5 mM EDTA) prior to exposing it to conditions that result in the cleavage of said riboprimers from said target DNA. A range of cleavage conditions capable of cleaving a bond between a deoxynucleotide and a ribonucleotide, thereby leading to the separation of riboprimers from both strands of a target DNA molecule, may be selected. In a preferred embodiment, the cleavage of the primers from a target DNA is achieved by incubating the target DNA with an RNAse that is capable of cleaving a bond between a deoxynucleotide and a particular ribonucleotide that was used in the primers. For instance, when a riboprimer comprises a riboC, any RNAse capable of cleaving a bond between a deoxynucleotide and a riboC may be used. Preferably, bovine pancreatic RNAseA is used to cleave the bonds between a deoxynucleotide and riboC, riboU, or riboT, and RNAseT$_1$ is used to cleave the bonds between a deoxynucleotide and a riboG. The amount of RNAse depends on multiple factors, such as, e.g., the amount of the target DNA, and can easily be determined by one of ordinary skill in the art. If the continued presence of the RNAse is detrimental to the eventual transformation of living cells or other immediate manipulation of the target DNA, a protease such as proteinase K is added to inactivate the RNAse and any other nucleases that may contaminate it. The incubation with protease is followed by heating the solution comprising the target DNA and RNAse, thereby releasing the riboprimers from the double-stranded DNA molecules.

In one embodiment, the riboprimers are specified and manufactured to contain a biotin moiety at their 5'-ends. In this case it improves the overall procedure to bind the PCR product to streptavidin beads at this time, which binding requires high salt, such as 0.25 M NaCl. Whether or not streptavidin beads are used, high salt such as 0.25 M NaCl is preferable at this time in order to control and achieve the melting of the primer portion of the molecule without melting the entire molecules. The temperature that results in melting off the riboprimers needs to be selected so that it does not have any negative effects on target DNA molecules, such as, e.g., denaturation. For instance, heating the solution to 75° to 85° C. will result in release of the riboprimers without denaturation of target DNA sequences. Other temperatures might be suitable, and can be determined by a skilled artisan. As a result of such cleavage and heating, the target DNA will contain 3'-overhangs, thereby creating a target DNA molecule with "sticky ends". A generation of a target DNA molecule containing 3'-overhangs is depicted in FIG. 2.

RNAse may be degraded by adding a proteinase to a solution comprising the target DNA and RNAse. Preferably, the RNAse is removed by the proteinase K. While removal of RNAse is not essential for the linking of nucleic acids as described herein, introduction of linked nucleic acids that also contain RNAse into cells chosen for transformation may be lethal to the cells under many circumstances. Therefore, it is preferable for transformation of cells with at least two DNA molecules that were annealed as described herein to remove or inactivate RNAse.

Additional methods of cleaving DNA/RNA bonds, such as exposure to elevated pH (e.g. treatment with a base such as sodium hydroxide) could also be employed to create target DNA sequences with 3'-overhangs. Unfortunately this base treatment will completely denature the vector and target DNAs. It is possible to reanneal to recover double-stranded target and vector DNA in this situation, and we have successfully created desired recombinant molecules this way. We find it much less efficient and productive, however.

It should be noted that the length of a 3'-overhang corresponds with the length of the riboprimer if a single ribonucleotide at the 3' end of the primer is used, or with the position of the most 3'-ribobase, if more than one ribobase is used. As mentioned previously, a preferred length of resulting sticky end is about 25 nucleotides; however other lengths can also be used. Moreover, the 3'-overhangs at the two ends of the target DNA need not have the exact complete same sequence or length. It is often desirable to generate a target DNA that can be annealed to a second DNA molecule in only one orientation or that can be annealed to two different DNA molecules in a particular arrangement. It is essential, however, that any two DNA molecules that are to be joined possess 3'-overhangs that are at least complementary in part. In cases of partial complementarity, it will be appreciated that following annealing, one or more gaps or non-homologous overlaps may be present in the joint sequence. As applicant has determined, the presence of one or more gaps did not negatively affect the efficiency of cell transfection with such annealed sequences (data not shown). While not being bound to a particular theory, it is believed that annealed sequences containing gap(s) are corrected after being introduced into the cells through actions of cellular enzymes involved in correcting DNA damage.

Any vectors available in the art may be used, subject only to their successful amplification by long and accurate PCR (LA PCR, U.S. Pat. No. 5,436,149), which can amplify up to at least 35 kb. Accordingly, depending on the organism in which they will be replicated, vectors may be selected from the group consisting of bacterial, yeast, viral, plant, and mammalian vectors. Both cloning and expression vectors may be used due to the fact that they contain nucleotide sequences that allow the vectors to replicate in one or more suitable host cells. In cloning vectors, this sequence is generally one that enables the vector to replicate independently of the host cell chromosomes, and also includes either origins of replication or autonomously replicating sequences. Various bacterial and viral origins of replication are well known to those skilled in the art and include, but are not limited to, the colE1 plasmid origin, the 2µ plasmid origin, and the SV40, polyoma, adenovirus, VSV and BPV viral origins. Common promoters used in expression vectors include, but are not limited to, CMV promoter, LTR or SV40 promoter, the *E. coli* lac or trp promoters, and the phage lambda PL promoter. Other promoters known to control the expression of genes in prokaryotic or eukaryotic cells can be used and are known to those skilled in the art. Expression vectors may also contain a ribosome binding site for translation initiation and a transcription terminator. The vector may also contain sequences useful for the amplification of gene expression.

Expression and cloning vectors can and usually do contain a selection gene or selection marker. Typically, this gene encodes a protein necessary for the survival or growth of the host cell transformed with the vector. Examples of suitable markers include neomycin or hygromycin B resistance for eukaryotic cells and tetracycline, ampicillin, or kanamycin resistance for *E. coli*.

The target DNA and vector DNA with single-stranded complementary 3' overhangs are then incubated together under conditions that result in annealing of their complementary overhangs. Exemplary conditions include incubation of the target and vector at 78° C. for 2 minutes, followed by an incubation at 52° C. for 30 minutes. Alternatively, the incubations can be the following: incubation for 2 minutes at 78° C. followed by 10 minutes at 65° C., followed by slow cooling e.g., over a period of 30 minutes to 52° C. and then chilling. One of ordinary skill in the art can determine other incubation conditions without undue experimentation. In fact, mere incubation at room temperature works pretty well. Additional modifications for optimizing the annealing rates between the vector and the target DNA may also be employed. Adjusting the salt concentration and temperature play a role in the annealing process, and thus might require optimization for different DNA sequences. Such modifications are well known in the art. It is preferred that annealing is performed at equimolar concentrations of the DNAs to be recombined, such as the target and vector DNAs.

In a further embodiment of the present invention, two or more double-stranded molecules may be linked, thereby generating a hybrid DNA molecule, when neither molecule is a vector per se.

It is preferred that different 3'-overhangs are generated when linking more than two DNA sequences. This allows for joining of DNA molecules in only one orientation, minimizing the screening process for a properly linked hybrid DNA, unless a random mixture of orientations and/or map arrangements is one of the desired outcomes. Furthermore, in such complex liking reactions, different 3'-overhangs help to minimize the possibility of self-annealing by individual sequences.

In yet another embodiment of the present invention, the linking reaction can include the use of biotin and streptavidin. Both the linking of a vector and a target DNA or lining of more than two DNA sequences may be performed using this method. Briefly, the generation of desired DNA molecules with complementary 3'-overhangs is performed as described herein by exposing said DNAs to conditions that result in cleavage of primers from the DNA molecules. The primers, in addition to containing at least one ribonucleotide at or near the 3' end also contain a biotin moiety at the 5' end. Primers modified in such manner may be obtained commercially (e.g. IDT) or riboprimers may be coupled to biotin. Methods for effecting the attachment of the hapten binding ligand (such as biotin) to the support (such as streptavidin beads) are described by Hevey et al. (U.S. Pat. No. 4,228,237) and by Kourilsky et al. (U.S. Pat. No. 4,581,333). When biotin is employed, a paramagnetic streptavidin conjugated bead, obtained from Genovision, Inc. (West Chester, Pa.) or Life Technologies, Inc. (Gaithersburg, Md.) or the Dynabead Streptavidin M-280 bead obtained from Dynal (Great Neck, N.Y.) can be used as the support. Other hapten-support systems may also be used.

The cleavage of the primers from the desired DNA molecules may not be 100% efficient. Accordingly, there likely will be DNA molecules that have not been cleaved and do not possess 3'-overhangs in the solution comprising target DNAs and primers. Such molecules cannot be linked by annealing to desired cleaved DNAs. In addition, cleaved primers and possibly primers left over from the PCR will also be present in the solution to compete for the desired annealing at the 3'-sticky ends. Despite best efforts to use a pure RNAse, in the absence of free magnesium, some of the 3'-sticky ends may be subject to damage or removal by unwanted nuclease activities, leading to another source of unsuitable ends. To increase the efficiency of linking two or more DNA sequences, it is generally desirable that only the sticky-ended vector and target(s) sequences be present in the annealing reaction.

To maximize the purity of cleaved DNAs before using them in the annealing process, the cleaved target DNA with biotin primers still on it, possible uncleaved target DNA, the possible loose primers, and proteinase K used to inactivate the RNAse, may be incubated in the high-salt annealing buffer with magnetic streptavidin beads. Proteinase K does not seem to hurt the beads, since strepatavidin is resistant to protease, particularly in the high-salt buffer necessary to get the beads to bind the biotin-PCR product. This incubation at i.e. room temperature results in binding of the biotin-containing molecules to said magnetic beads, then unbound material is washed away, then more annealing buffer is added. In the next step, the beads are heated to around 75-85° C. to melt off desired DNA away from the primers and uncleaved DNA which remain stuck to the beads at their biotin moeities, and a after a few minutes a magnet is applied near to the solution containing the cleaved DNA, biotin-labeled DNAs, and streptavidin beads, thereby separating the cleaved target DNA molecules from the uncleaved, biotin-labeled ones and from unwanted contaminating primer. The use of the magnet allows for the beads to be immobilized while the solution containing the desired pure DNA is withdrawn. It should be noted that normally each DNA target or vector is separately treated with streptavidin beads. The target and vector DNA sequences are then storable in the freezer, and may be, when desired, mixed together at preferably equimolar amounts and incubated under conditions that result in annealing of the complementary ends thereof.

Alternatively, but not preferably, the DNAs are allowed to affix to the streptavidin beads before the scission at the ribonucleotides and the proteinase K treatment. Proteinase K does not seem to hurt the beads, since streptavidin is resistant to protease. Following the amplification of desired DNA molecules using primers comprising at least one ribonucleotide at their respective 3' ends and a biotin at their respective 5' ends, the DNAs and the primers can be incubated with streptavidin beads. Following such incubation, the solution comprising said beads, DNAs and the primers is exposed to conditions that result in the cleavage of said primers from the DNAs, leading to the generation of cleaved DNAs that are free in solution, while uncleaved DNA molecules and the primers stay attached to the beads. The magnet is then applied to the solution in order to separate the beads with attached biotin-containing molecules from the solution. Following separation of the beads, the desired DNA molecules are combined at preferably equimolar ratios and incubated under conditions that result in annealing of their complementary ends.

Any two or more linked DNA sequences can then be propagated in cells, subject to the normal requirements of replication (including recombinational insertion into a genome) and marker selection. Introduction of such sequences, i.e. transformation into cells, can be achieved by any of the methods available in the art. Such methods include, but are not limited to, calcium phosphate transfection, DEAE-dextran mediated transfection, Polybrene mediated transfection, protoplast fusion, liposome mediated transfection, direct microinjection into the nuclei biolistic (gene gun) devices, scrape loading, electroporation, and calcium and lithium treated bacterial cells.

The following examples illustrate the invention, but are not to be taken as limiting the various aspects of the invention so illustrated.

EXAMPLES

Example 1

Most of these incubations are programmed into a PCR i.e. thermocycler machine, with "chill" being hold on cold block for 5 min. to overnight.

*E.coli* X7029 is F- and wild-type except for a lac-pro deletion.

*E.coli* WB451 (IDE3) is a deletion of lacZ codons, constructed by the method of Datsenko and Wanner. (Datsenko, K. A., and Wanner, B. L. One-step inactivation of chromosomal genes in *Escherichia coli* K-12 using PCR products. Proc.Natl.Acad.Sci. USA 97:6640-6645, 2000.) and it is lysogenic for lambda DE3 transducing phage. There is nothing about the *E. coli* cells used here that is particular or necessary to the method, as far as is known or expected.

Bacteria are made electrocompetent and transformed by electroporation as described by Dower, W. J., Miller, J F. and Ragsdale, C. W. (1988) High efficiency transformation of *E.coli* by high voltage electroporation, *Nucleic Acids Research* 16:6127-6145 and Mattanovich, D., et al, (1989) Efficient transformation of *Agrobacterium* spp. by electroporation, *Nucleic Acids Research* 17:6747.

When DpnI treatment was employed, background transformation with vector alone or target alone was always less than 1%, usually less than 0.1%, of the recombinant clones.

10×ATEN buffer is (0.5 M Tris pH 7.9, 2.5 M NaCl, 0.25 M Na4EDTA pH 7.9). Add ⅑ volume to make 1×.

T005,E005 is 5 mM Tris pH 7.9, 5 mM Na4EDTA pH 7.9.

TEN is 10 mM Tris pH 7.9, 0.1 mM EDTA, 10 mM NaCl.

10×KLA pH9.2 is 500 mM Tris base, 160 mM ammonium sulfate, 25 mM MgCl2, 1% Tween 20.

10×KLA pH7.9 is the same as 10×KLA pH9.2 except that HCl has been added to lower the pH.

1. Amplify target and vector using KlentaqLA DNA polymerase mixture and ribo-U or ribo-C at the 3'-ends of the primers. Four PCR conditions should be evaluated: KLA buffer pH 7.9 or pH 9.2, and betaine at 1.3 or 1.9 M. For best cloning efficiency, additionally specify 5'-Biotin or 5'-Biotin-TEG modification for the primers, and use streptavidin beads as described below in Example 2. Additional PCR details are 100 uM each dNTP, and 0.1 ul KlentaqLA per kb of amplimer size, up to 10 kb (Barnes, 1994).

Dpn I selection. If the template for the vector or the target came from dam+ *E.coli*, and could contribute to an unwanted background later at the cloning step, degrade the background template at methylated GATC sites: To each 100 ul of PCR reaction, add 1 ul (10 units) of DpnI, and incubate 37 degrees for 1-2 hours.

2. PEG-precipitate the DNA. This is to lose the primers and the salt. The desired DNA will be in the pellet.

Transfer to thick-walled (regular-walled) tubes, either 0.5 ml or 1.7 ml, for this. Thin-walled PCR tubes cannot reliably withstand the centrifuge step.

Add 5 ul 1 mg/ml blue dextran and ½ volume 30% PEG 3350, 1.5 M NaCl (to make final 10% PEG, 0.5 M NaCl).

Wait 30 min. at R.T. or 90 min. to overnight at 4 degrees. Centrifuge 15 min. Watch blue pellet whilst removing supernatant, so as not to accidentally discard the pellet. Rinse pellet with 75% ethanol (centrifuge 8 minutes).

Dry pellet for 10-20 minutes in air. Resuspend in 100 ul T005,E005 for at least 10 minutes on ice, with vortexing occasionally.

3. Pancreatic RNase A: Dilute some Ambion 2270 or 2272 RNAse A to a concentration of 200 ug/ml in T005,E005 buffer. May be stored frozen.

Add 6 ug (30 ul) RNAse to the DNA on ice. Vortex and centrifuge briefly, then incubate PCR products with RNAse for 30 min. at 55 degrees. Chill.

4. Proteinase K: Stock be stored at −20 degrees in 100 mM beta-mercaptoethanol, 20 mM Tris pH 7.9, 1 mM CaCl2, 50% (v/v) glycerol.

Add 5 ug proteinase K or about equal the weight of RNAse used above. Mix thoroughly and spin briefly.

Incubate 30 min. 65 degrees, chill.

[If using biotin primers, go now to bead purification steps in EXAMPLE 2 below, then come back here.]

5. Cloning Step

Double-check target and vector DNA concentrations by loading 2 and 8 ul samples of each vector or target onto agarose gel alongside a concentration standard. The exact concentration is not as important as getting the ratios to be equimolar for the cloning.

01 to 10 ul vector=30 ng 0.02 pmole 01 to 10 ul target=5 ng (Equimolar is best for target:: vector.)

10×ATEN to make 1×, if necessary

1×ATEN to 40 ul.

6. Use 20 ul aliquots of cloning mix for various controls, such as before heating, no heating, gel samples, etc. So make up more of the cloning mix as necessary, in proportion. Minimum is 40 ul: 20 ul for gel, 20 ul for transformation of cells.

The best control is a 20 ul aliquot with the 2 vector primers (or the 2 target primers) added in the amount of ½ to 5 pmole of each. This will poison the ends and make the annealing impossible—this gel (and/or transformation) sample will show you what the input DNA looks like with no annealing. This is analogous to a no-ligase control for prior art methods using restriction sites.

Another good control is to include only one poison primer—this control will show you what lousy annealing looks like, although sometimes when it looks like this there are still hundreds of good clones that arise from an invisible circular product band.

7. Annealing may not be necessary for bead-purified DNA, but for non-biotin primers, this heat step helps a lot.

Incubate 2 min 78° C., 30 min. 52° C. Alternatively, 2 min. 78° C., 10 min 65° C., then cool slowly over 30 minutes to 52° C. or lower. Chill.

Pull aliquot (20 ul) for after-annealling gel sample.

These gel samples are for monitoring and improving the recombination. These gel samples may be skipped for routine cloning, but, as for any DNA cloning experiment, if something goes wrong, you won't know what it was without the gel analysis. If you didn't run the gel samples, don't ask someone else what went wrong; they won't know either. If you did run the gel samples, you will probably be the expert.

8. Add ⅑ or ⅙ volume 3 M sodium acetate, pH 5.6, and 2 mg blue dextran. Add 2-3 volumes ethanol to precipitate, chill to −20 degrees for 30 min, and centrifuge 10-15 min. Rinse the (hopefully visibly blue) pellet with 75% ethanol: 25% TEN buffer—centrifuge 8 min.

9. Resuspend dry pellets in 22 ul water on ice. Water should turn slightly blue from the blue dextran carrier. Save 7 ul for a gel sample or a backup transformation.

10. Electroporate 70 ul competent bacteria with 15 ul DNA. Plate a suitable portion on Ticarcillin 100 after 10 minutes or on Kan25 after 5-16 hours or on Tet12 after 2 hours. The above is just one way to work up the PCR products with RNAse treatment. There are alternate ways to purify PCR products free of primers, treat them with enzyme(s), and remove the enzyme(s).

Example 2

Paramagnetic Streptavidin Bead Way

1. Amplify target with 5'-Bio-TEG and 3'-riboC primers.

DpnI, PEG-precipitate, RNAse and proteinase K in T005, E005 as in Example 2. above.

Add ⅑ volume of 10×ATEN buffer to make samples 1×ATEN.

Pre-preparation of beads: Withdraw a volume of resuspended beads from their storage tube, magnetize, and discard the storage buffer. Wash twice (including once at 80 deg with 5-10 minute soak) with the same volume of 1×ATEN buffer. Resuspend in 1×ATEN buffer for use, and store at 4 deg. for up to at least 2 weeks. This washing is to remove loose streptavidin. The proteinase K, if left over, does not hurt the streptavidin beads.

2a. To each amount of DNA that originates from 130 ul of PEG-precipitated PCR reaction add 60 ul of Genovision beads previously pretreated and resuspended in 1×ATEN buffer as above. Incubate 30 min. 25 deg. with occasional shaking.

Magnetize, and save the bead supernatant "B.S."

2b. If significant amounts of DNA do not stick to beads in 1×ATEN (i.e. are in the B.S.), try adding 1 pmole of one biotin primer to the (bead-free) DNA, and anneal at 52 degrees for 30 min. Then add more beads as for 2a.

3. Wash DNA-containing beads once or twice quickly with 200-500 ul 1×ATEN. This is to remove more initial PCR template and RNAse.

4. Heat-elute at 80 degrees 2 or 3 times with 100 ul 1×ATEN as follows:

Heat at 80 deg. for 3-5 min. Move tubes to 80 deg. hot block holes with a magnet in them for another few minutes.

One at a time, hold warm tubes next to magnet in hand and withdraw supernatant. This is the ribocloning DNA.

Pool the 2 or 3 elutant volumes, and magnetize or centrifuge it one more time to remove all traces of beads.

5. DNA is now ready for cloning. The DNA is now in 1×ATEN, so make sure final ATEN is 1× during the recombination annealing described in step 5 of Example 1.

Equimolarity is very important to a good yield of recombinants, so remeasure the quantities of DNA: Load 2 or 8 ul onto a gel next to 2 or 8 ul of lambda+H3 digest to quantitate vector and target DNA. Recombine as described in step 5 of Example 1. above.

Yield: With *E.coli* X7029, which is not particularly electrocompetent (10**8 per ug plasmid), we get 1,000-3,000 clones per ul (10 ng) of original target PCR reaction. X7029 has wild-type recombination. With JC8679, which is more electrocompetent and has high RecET activity, there are 10× more colonies, but an unacceptable portion of these are unwanted recombinants or rearrangements between repeated spans of our vector and/or target.

Example 3

Ribocloning an Artificial Ds-Red Gene and the Gene for Taq DNA Polymerase.

The specific vectors and targets are presented as arbitrary examples, only. The method is highly general and does not depend on any specific target or vector. Undue experimentation is not required to adapt the method to nearly any vector, and to nearly any site within any vector, that may be chosen by a practitioner of the art, nor to nearly any target. The only requirement is that the PCR amplification work well. Usually, the exact desired and chosen site within a desired vector, and the exact span of desired target, may be recombined using the method.

Riboprimers used in the examples are listed here, in standard 5'-3' sequence. The last and lower case letter represents the 3'-ribo base. These primers names are used in the Sequence Listing, also.

```
T7gen10rC  = GTTTAACTTT AAGAAGGAGA TATAc

T7gen10atrC = GTTTAACTTT AAGAAGGAGA TATATc

T41 = GTG GCG AGA AAG GAA GGG AAG AAA Gc

V01neg7T = GTATATCTCCTTCTTAAAGTTAAAc

V41 = GCTTTCTTCCCTTCCTTTCTCGCCAc

T7gen10rU = GTTTAACTTTAAGAAGGAGATATAU
```

5'-biotin modification was sometimes specified at the 5'-end when ordering from IDT (Integrated DNA Technologies, Coralville, Iowa), with or without TEG linker. Primerfinder (http://eatworms.swmed.edu/~tim/primerfinder) was used to design primers T41 and V41, which are in the phage fl DNA portion of the plasmid vector.

Vector PCR. Two vectors are shown in FIG. 2. Ribovector 250, 4.8 kb: Template for PCR was pWB250 digested with HindIII and NcoI. The same ribovector 250 DNA would have arisen if the template were pWB254b (ATCC #69244) linearized by digestion with NcoI. When amplified using PCR riboprimers V01neg7TrC and V41, the product is equivalent to the backbone of pWB254 described in U.S. Pat. No. 5,436,149, with base pairs 2217 to 4138 missing, nucleotide 2218 (the first one of V01neg7TrC) changed from an A to a G, and a single ribonucleotide rC at 25 or 26 bases from each 5' end, at positions 2194 and 4164.

Ribovector ASK75 PCR, 2.9 kb: Template was pASK75 [Skerra, A. Use of the tetracycline promoter for the tightly regulated production of a murine antibody fragment in *Escherichia coli. Gene* 151 (1994) 131-135.] digested with EcoRI and HindIII. The same PCR riboprimers were used as above for ribovector 250, with the addition of one band-aid primer to adapt the V01neg7TrC to prime, and change the Shine-Dalgarno site to that of gene 10 from phage T7. That band-aid sequence, included at only 10 nM for the PCR, was ASK-T7SD, A CTCCCTATCA GTGATAGAGA AAAGT TTAACTTTAAGAAGGAGATATAC.

Target PCR. Two targets are shown being cloned in FIG. 2. Ribotarget maize Ds-Red PCR, 1 kb: Template was pWB397, which is a clone of an artificial gene assembled from 40-mers by the method described in this patent. It was cloned into the ribo-vector form of pWB250 using a riboprimer somewhat differently located than T41. The riboprimers T7gen10rC (2194-2218 of pWB397) and T41 (3174-3149 of pWB397) give rise to a 1 kb product (981 bp) which comprises a 678 bp ORF of a artificial codons which code for Ds-Red. The product comprises a riboC at a position 26 bases from each 5'-end.

Ribotarget Taq DNA Polymerase gene, 2.5 kb. Template was genomic DNA from Thermus aquaticus i.e. ATCC #25105. Primers were T7gen10atrC, and T41. Included in the PCR at 10 nM were 2 band-aid oligomers to adapt the PCR primers to prime the target. These band-aids were "T7SD-Q5 band-aid" GTTTAACTTT AAGAAGGAGA TATATCCATG AGaGGGATGC TGCCCCTCTT TGA (contains a change to 2d codon (for ARG) to break up a run of G5)

and

"T41-Q3 bandaid" GTG GCG AGA AAG GAA GGG AAG AAA GCT CAC TCC TTG GCG GAG AGC CAG TCC T PCR conditions were as described in Example 1 and 2, with the following details.

Reaction volume was 150 ul. Melt time per cycle was 70 seconds at 93 degrees C. One other temperature was used per cycle: 62 degrees to anneal/extend. The time of extension was 20 minutes if one or more band-aids were included; otherwise the 62-degree time was 10 minutes. The vector and target products were amplified, worked up to the 3'-sticky-ended forms, mixed and annealed by the methods of Example 1 and 2.

Example 4

This example demonstrates ribocloning the Taq gene without or with bead purification, and using beads but comparing with or without proteinase K treatment, using a ribovector with an assembled portion.

In this example, the vector was ribovector 419. To prepare this ribovector by PCR, a cluster of four 42-mers was included in the PCR reaction at 10 nanomolar to assemble a 80 bp span of DNA, containing a T7 promoter and ribosome binding site region, onto the plasmid where it did not exist before. Our normal vector riboprimer V01neg7TrC could then, present at the normal level for PCR (200 nM) prime onto the end of this assembled region. At the other end of the ribovector PCR amplimer, our vector riboprimer V41 required the presence of a 50-mer bandaid to adapt priming. Despite this seeming complexity, this is a very reliable PCR amplification that we have carried out several times, including with templates pKD46 and pKD911.

The four 42-mers that assembled 104 bp for the new phage T7 control region are listed below. The first 25 bp of the resulting assembly are homologous to bp 1210-1234 of pKD46 (Datsenko & Wanner, 2000) in order to overlap for the PCR amplification; thereafter the sequences is from phage T7 right before gene 10.

```
;pKD46-T7 42mer
TTTGGGAATTCGAGCTCTAAGGAGGTTAATACGACTCACTAT

;T7Iea 42mer
AGGGAGACCACAACGGTTTCCCTCTAGAAATAATTTTGTTTA

;V01neg7Tbot 42mer
GTATATCTCCTTCTTAAAGTTAAACAAAATTATTTCTAGAGG

;T7Ieabot 42mer
GAAACCGTTGTGGTCTCCCTATAGTGAGTCGTATTAACCTCC
```

The bandaid to allow riboprimer V41 to prime onto pKD46, or pKD119 (analogous to pKD46 but having tetracycline resistance in the place of, and in the opposite orientation to, ampicillin resistance; B. Wanner, personal communication), is "exoCt'-T41"GGA TGC GTC ATC GCC ATT GCT CCC CGT GGC GAG AAA GGA AGG GAA GAA AGC Adjacent to complementarity for V41/T41, this band-aid incorporates complementarity to 3111-3135 of pKD46 and pKD119.

Thus, the vector PCR reaction included, per 100 ul, 1 pmole of the above 5 oligomers, 20 pmoles of 5'-biotin V41, and 20 pmoles of 5'-biotin V01neg7T. The template was 10 ng of pKD119 pre-digested with Pst I.

The target DNA was ribotarget Taq gene (2.5 kb) prepared as described in Example 3.

FIG. 5 shows the results when target and vector were prepared and mixed together for cloning according to Example 1, with no bead purification having been used. It can be seen that heating is required to obtain fused target and vector since without it (lane 1) target and vector migrate separately. After heating and annealing, a new upper band appears. This is not actually the desired circular fusion of target and vector. The yield of said desired product, the circular fusion, is so poor that it does not appear visible on this gel (it would migrate between bands 1 and 2 of the standard lane, as can be seen from the more successful experiment shown in FIG. 4). Another suboptimal feature of this riboocloning, i.e. a slight error, is that the ratio of vector to target is quite far from equimolar—there is too much target. Nevertheless, although the desired product band was too low in yield to be visible, valid recombinant clones were obtained. As enumerated in Table 2, about 14 colonies were obtained per ng of vector DNA, and as assayed in FIG. 6, rows 1 and 5, 19 of 24 clones exhibited the desired activity of thermostable DNA polymerase.

FIG. 4 shows a more advanced and successful cloning. The same target (Taq gene) and vector (V419, a.k.a. pWB419, amplified from pKD119 template) preparations were used, but subjected, before cloning, to the streptavidin bead purification described in Example 2. Also, the necessity of the proteinase K step was tested by leaving it out of the target and vector DNA preparations loaded onto the right half of FIG. 4. In lane 3, combined target and vector were allowed to sit at room temperature for one hour, without a heating and annealing treatment. Lanes 4, 5, and 6 (labelled P1, p2 and CL) were subjected to the heating and annealing treatment. To illustrate poor cloning efficiency (such as that for FIG. 5), one poison primer was included in the annealing loaded in lane 4 (P1). To illustrate no annealing at all, and so that the input DNAs could be separately visualized and confirmed in the production annealing mixture, two poison primers were included in the annealing loaded in lane 5 (P2), as recommended in Example 1. and as indicated on the FIG. 4. The material analyzed in the lanes marked CL was transformed into *E. coli*, and the quality of the clones was confirmed in the assay shown in FIG. 6. Again, at least 80% of the clones exhibited the desired thermostable DNA polymerase activity. Many more clones were obtained with this bead-purified DNA, as enumerated in Table 2. About twice as many clones were obtained when proteinase K treatment was not omitted from the recommended procedure. In early experiments with target and vector that were not purified with streptavidin beads, and using less pure RNAse A, the importance of proteinase K was much higher: proteinase K treatment improved transformation by 100-fold (data not shown.)

LIST OF FIGURES

FIG. 1. Schematic of the ribocloning method.

FIG. 2. Three example riboclonings analyzed by agarose gel.

FIG. 3. Transformant *E. coli* colonies arising from ribocloning a gene encoding Ds-Red protein.

FIG. 4. Variations on ribocloning the Taq Pol I gene for Thermus aquaticus DNA polymerase, using bead-purifed DNA.

FIG. 5. Cloning the Taq Pol I gene without using bead-purified DNA.

FIG. 6. Assay of clones of Taq Pol I gene to confirm successful cloning of active genes.

TABLE 1

| Sizes of DNA loaded onto the agarose gels, in base pairs (bp). | | |
|---|---|---|
| 23130 | Standard band 1 of lambda + HindIII digest. | |
| 9416 | Standard band 2 | |
| 6557 | Standard band 3 | |
| 4361 | Standard band 4 | |
| 2322 | Standard band 5 | |
| 2027 | Standard band 6 | |
| 564 | Standard band 7 | not always visible |
| 4798 | Vector 250 | amplifiable from pWB254 or pWB250 |
| 4997 | Vector 419 | amplifiable from pKD119 |
| 2913 | Vector 75 | amplifiable from pASK75 |
| 2552 | Target Taq Pol I gene | amplifiable from genomic Taq DNA |
| 981 | Target Ds-Red gene, artificial codons | amplifiabie from pWB397 |

TABLE 2

Yield of clones.

| Workup after RNAse | 50 ul actual colony count | Total projected colony yield if all plated. | Transformants per ng vector DNA |
|---|---|---|---|
| P-k, no beads (gel FIG. 5) | 27 | 850 | 14 |
| Beads & P-k (Left of FIG. 4. gel) | 550 | 17,000 | 283 |
| Beads, no P-k (Right FIG. 4. gel) | 281 | 8700 | 144 |
| Super-coiled plasmid | | | 30,000 |

DESCRIPTION OF FIGURES

All agarose gels (FIGS. 2, 4 and 5) contain a standard lane in which was loaded phage lambda DNA digested with restriction enzyme HindIII. The band sizes, in order from the top, are, if they are visible, are shown in Table 1.

FIG. 3. Clones arising from ribocloning the Ds-Red gene, from the cloning/annealing depicted in lane 1 of FIG. 2. Bright red colonies are the desired clones, expressing Ds-Red as a pigment in this E. coli bacterial background after one week on the plate. Colorless colonies are the 10% typical misclones with this method. The cause and nature of the misclones is unknown at this time, but their number is too high to be PCR-induced mutations under the high-fidelity PCR conditions employed. Off-color clones (pink or orange) are presumably PCR-induced mutations. Some colonies have been smeared with a toothpick when picked for further analysis.

FIG. 4. Ribocloning the Taq gene demonstrating the use of streptavidin bead-purified vector and target DNA, and demonstrating the use of proteinase K. After the RNAse A treatment with USB RNAse (not of the preferred purity, which is Ambion 2270), proteinase K treatment was included as normal for the samples on the left, but omitted for the right side samples, before high-salt adsorption to and heat-elution from paramagnetic streptavidin beads. "LINE" marks a band which is believed to be a linear combination of one target and one vector molecule. This molecule it not the desired endpoint which is capable of efficient transformation of cells. "CIRCLE" marks the position of a band that is believed to be the desired endpoint of the recombination. The number of transformant colonies from the method is greatest when this band is visible and prominent. The method was followed according to Example 1 and Example 2, except that on the right side of the gel, proteinase K treatment was omitted. See Table 2 for colony counts.

Figure 1:
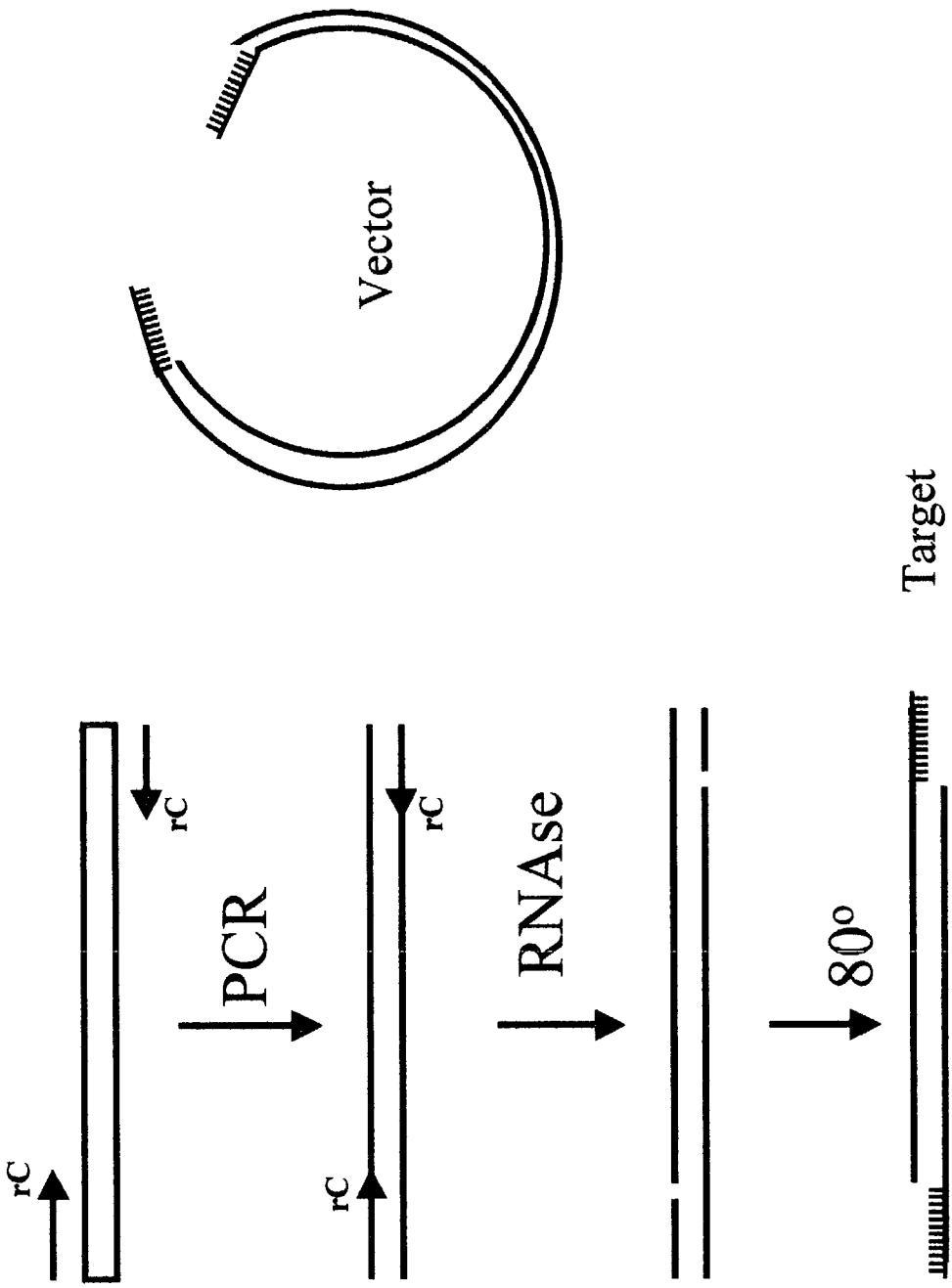
FIG. 1. Schematic of the ribocloning method. Riboprimers are PCR primers with at least one ribo base at the 3'-end. The depicted example primers have a 3'-ribo C. DNA depictions, primers and resulting sticky ends are not to scale. Processed form of target has ca. 25-base 3'-sticky ends. Vector, made with same steps but with complementary riboprimers, has specific complementary sticky ends.
Figure 2:
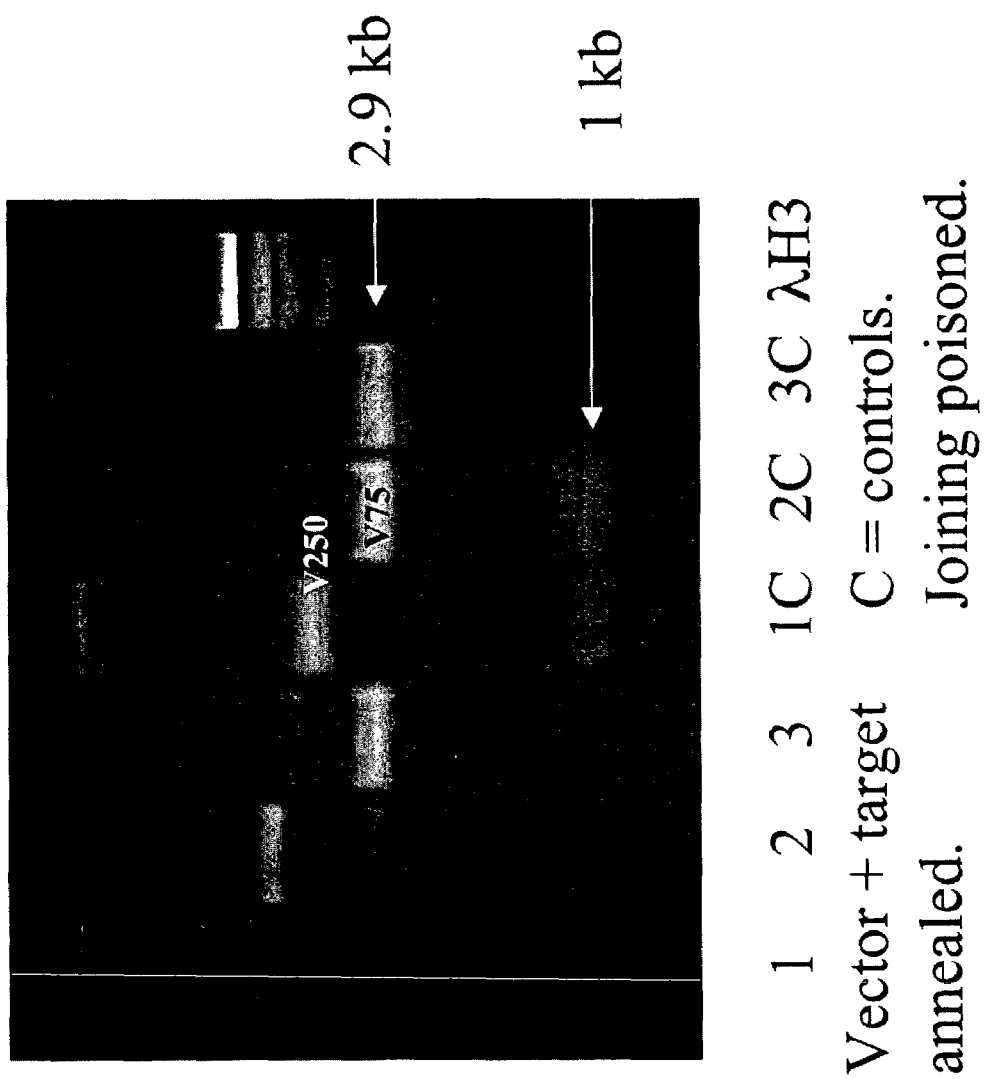
FIG. 2. Three cloning experiments are shown. Experiment 1, 2, and 3 annealed DNAs are shown in lanes 1, 2, and 3. Lanes 1C, 2C and 3C, respectively, show the input DNAs migrating separately. To get this effect, vector primers V01neg7T and V41 were included to poison (prevent by competition) the annealings. Experiment 1 vector was Ribovector 250, labelled "V250". Experiment 1 and 2 target was ribotarget maize Ds-Red. Experiment 2 and 3 vector was Ribovector ASK75, labelled "V75". Experiment 3 target was the Taq DNA polymerase gene, which was inadvertently included at lower than recommended equimolar, at such a low level that it is not visible on this fuzzy gel. The experiments in lanes 1 and 2 utilized a vector:target input ratio which was much closer to the ideal of equimolar.

V=Vector PCR product pWB419.

T=Target PCR product Taq pol ORF.

C=Heating and annealing omitted.

P1=Primer T41 included to poison one end.

P2=Primers T41 and V01neg7T included to poison two ends.

CL=Complete cloning procedure with heating and annealing.

Std=Lambda DNA digested with HindIII.

FIG. 5. Ribocloning without the purification on streptavidin beads. This is an example of the many preliminary experiments which were done without streptavidin beads, and which served to establish the salt, incubation, and temperatures which are recommended throughout the Examples. Gel shows before (lane 1) and after (lane 2) annealing of vector (V) and target (T) mixture, neither bead-purified.

FIG. 6. Assay for thermostable DNA polymerase activity to confirm clones of Taq Pol I gene. This assay constitutes confirmation of successful cloning of the Taq Pol I gene as depicted in FIG. 4 and 5. Transformant colonies were grown on nitrocellulose and assayed by the method of Sagner et al, [Sagner G, Ruger R, Kessler C. (1991). Rapid filter assay for the detection of DNA polymerase activity: direct identification of the gene for the DNA polymerase from Thermus aquaticus. Gene 97:119-123] as modified and described by Barnes and Kermekchiev (U.S. Pat. No. 6,214,557). Each of 96 clones is assayed as a trio of inoculated spots of bacteria. A trio of visible spots indicates TCA-insoluble material incorporated by a positive clone at 65° C. Rows 4 and 8 are each assays of 12 clones that are invisible, because they are negative controls that are not expected to have any Taq DNA. Rows1 and 5 each assay 12 colonies from the cloning depicted in FIG. 5. Rows 2 and 6 assays 12 colonies from FIG. 4 right, and Rows 3 and 7 each assay 12 colonies from FIG. 4 left. As is typical for the method at this stage of development, some 10% of the Taq clones are in fact negative in this assay, such as the ones in row 1, column 2, and row 2, column 7; the nature of these apparent misclones has not yet been determined.

What is claimed is:

1. A method of cloning in vitro a double-stranded target DNA into a double stranded vector DNA, said method comprising:
   a) generating a double-stranded target nucleic acid molecule by extension of at least two target-specifying primers that each contain at least one ribonucleotide, at one or more positions within at most 5 nucleotides from a 3'-end, wherein the first target-specifying primer is complementary to a first vector-specifying primer that would direct amplification of vector; the second target primer is complementary to a second vector-specifying primer; and the extension of primers is performed using a polymerase mixture comprising (i) an Archael polymerase and (ii) a Taq polymerase, a Klentaq polymerase, or Taq polymerase and a Klentaq polymerase; and
   b) contacting the target DNA and an RNAse so as to cleave a phosphodiester bond between a ribonucleotide and a deoxyribonucleotide in a double stranded nucleic acid and to generate a cleaved target DNA with 3'overhangs;
   c) providing a double-stranded vector DNA with 3'-overhangs that are complementary to the 3'-overhangs of the cleaved target DNA; and
   d) incubating said cleaved target DNA and said vector DNA together under conditions that result in annealing of the complementary ends thereof to form a vector comprising the double-stranded target DNA;
   wherein,
      said cloning method does not require the use of a restriction enzyme, a restriction site sequence, a joining enzyme, or a topoisomerase to form a stable vector comprising the double-stranded target DNA that is capable of transformation into a host cell without further enzymatic processing in vitro; and
      the stable vector comprising the double-stranded target DNA formed in (d) is not contacted with a joining enzyme in vitro prior to use for transformation of a host cell.

2. The method of claim 1, wherein the ribonucleotide is at the 3'-end and is selected from the group consisting of riboA, riboC, riboG, riboU, ribo I, and riboT.

3. The method of claim 2, wherein the ribonucleotide is riboC or riboU and the RNAse is RNAse A.

4. The method of claim 1, wherein the RNAse is selected from the group consisting of RNAse A and RNAse $T_1$.

5. The method of claim 3 wherein the ribonucleotide comprises riboT and the RNAse is pancreatic RNAse A.

6. The method of claim 2, wherein the ribonucleotide at the 3' end of the primer is riboG and the RNAse is RNAse $T_1$.

7. The method of claim 1 wherein the extension of primers is performed using a DNA polymerase selected from the group consisting of Vent, Deep Vent, Pfu, Klentaq1, KlentaqLA, TaqLA, Taq, KOD, and mixtures thereof.

8. A method of claim 1 wherein a circular recombinant molecule is not sought, but rather two or more linear molecules are linked together and the product recombinant is linear.

9. The method of claim 4, wherein the primers have a length of 18-50 bases.

10. The method of claim 4, wherein the primers have a length of 22 to 33 bases.

11. The method of claim 4, wherein the primers have a length of 24 to 26 bases.

12. A method of generating cells comprising a chimeric DNA comprising a target DNA and a vector, the method comprising:
   amplifying a target nucleic acid in a polymerase chain reaction using a reaction mixture comprising an upstream primer comprising at least one ribonucleotide at one or more positions within at most 5 nucleotides from a 3'-end and a downstream primer comprising at least one ribonucleotide at one or more positions within at most 5 nucleotides from a 3'-end to generate a PCR reaction product comprising at least one ribonucleotide in each strand; and a polymerase mixture comprising (i) an Archael polymerase and (ii) a Tap polymerase, a Klentaq polymerase, or Taq polymerase and a Klentaq polymerase; and
   cleaving the PCR reaction product at the at least one ribonucleotide in each strand to generate a double stranded nucleic acid comprising 3' overhangs;
   annealing the double stranded nucleic acid comprising 3' overhangs with a vector comprising complementary 3' overhangs to generate an annealing product; and
   transforming or transfecting a population of host cells with the annealing product, wherein the yield of transformants or transfectants is greater than 100 transfected or transformed host cells per 10 ng of target PCR reaction product;
   wherein said cloning method does not require the use of a restriction enzyme, a restriction site sequence, a joining enzyme, or a topoisomerase; and
   the annealing product is not contacted with a joining enzyme in vitro prior to use for transformation or transfection of the host cells.

13. A method in accordance with claim 12, wherein the yield of transformants or transfectants is at least about 1,000-3,000 clones per 10 ng of target PCR reaction product.

14. A method in accordance with claim 12, wherein the population of host cells is a population of *E. coil*.

15. A method in accordance with claim 12, wherein the cleaving the PCR reaction product comprises digesting the PCR reaction product with at least one RNAse capable of cleaving a phosphodiester bond linking a deoxyribonucleotide and a ribonucleotide within a double stranded nucleic acid.

16. A method in accordance with claim 12, wherein the at least one RNAse capable of cleaving a phosphodiester bond linking a deoxyribonucleotide and a ribonucleotide within a double stranded nucleic acid is RNAse A, and wherein the upstream primer and the downstream primer each comprise at least one ribonucleotide selected from the group consisting of riboU, riboT and riboC.

17. A method in accordance with claim 12, wherein the at least one RNAse capable of cleaving a phosphodiester bond linking a deoxyribonucleotide and a ribonucleotide within a double stranded nucleic acid is RNAse $T_1$, and wherein the upstream primer comprising at least one ribonucleotide and the downstream primer comprising at least one ribonucleotide each comprise at least one riboG.

18. A method in accordance with claim 12, wherein the vector is selected from the group consisting of a bacterial vector, a viral vector, a yeast vector, a plant vector, and an animal cell vector.

19. A method in accordance with claim 1, wherein contacting the target DNA and the RNAse occurs in a solution comprising 5 mM Tris-HCl buffer at a pH of 7.9 and 5 mM sodium EDTA at a pH of 7.9.

20. A method in accordance with claim 1, wherein contacting the target DNA and the RNAse occurs in a solution comprising 10 mM Tris-HCl buffer at a pH of 7.9, 10 mM NaCl, and 0.1 mM EDTA.

21. A method in accordance with claim 1, further comprising the step of inactivating the RNAse after generation of the cleaved target DNA with 3' overhangs.

22. A method in accordance with claim 21, wherein inactivation of the RNAse comprises contacting the RNAse with a proteinase.

23. A method in accordance with claim 1, further comprising the step of isolating ribonucleotide-containing primers after generation of the cleaved target DNA with 3' overhangs.

24. A method in accordance with claim 23, wherein isolating ribonucleotide-containing primers comprises:
   contacting a cleaved target-specifying ribonucleotide-containing primer with a streptavidin to form a streptavidin-primer complex;
   and isolating the streptavidin-primer complex;
   wherein the target-specifying primers comprise a biotin moiety at a 5'-end of the primer.

25. A method of cloning in vitro a double-stranded target DNA into a double stranded vector DNA, said method comprising:
   a) generating a double-stranded target nucleic acid molecule by extension of at least two target-specifying primers with a length of 24 to 26 bases that contain at least one ribonucleotide at a 3'-end of the primer, wherein the first target-specifying primer is complementary to a first vector-specifying primer that would direct amplification of vector, and the second target primer is complementary to a second vector-specifying primer; and the extension of primers is performed using a polymerase mixture comprising (i) an Archael polymerase and (ii) a Taq polymerase, a Klentaq polymerase, or Taq polymerase and a Klentaq polymerase; and
   b) contacting the target DNA and an RNAse A or an RNAse $T_1$ so as to cleave a phosphodiester bond between the 3' ribonucleotide of the primer and a deoxyribonucleotide of the double stranded target DNA and to generate a cleaved target DNA with 3' overhangs;
   c) inactivating the RNAse with a proteinase after generation of the cleaved target DNA with 3' overhangs;
   d) isolating ribonucleotide-containing primers after generation of the cleaved target DNA with 3' overhangs;
   e) providing a double-stranded vector DNA with 3'-overhangs that are complementary to the 3'-overhangs of the cleaved target DNA; and
   e) incubating said cleaved target DNA and said vector DNA together under conditions that result in annealing of the complementary ends thereof to form a vector comprising the double-stranded target DNA;
   wherein a restriction enzyme is not used in said cloning method; and
   the vector comprising the double-stranded target DNA formed in (e) is not contacted with a joining enzyme in vitro prior to use for transformation of a host cell.

* * * * *